United States Patent [19]

Perjé et al.

[11] Patent Number: 4,659,712
[45] Date of Patent: Apr. 21, 1987

[54] FODDER ADDITIVE AND A PROCESS FOR THE PREPARATION

[75] Inventors: István Perjé; Lázló Szporny; András Selmeczi; László Vereczkey; Imre Klebovich; Edit Tóth; György Hajós; József Törley; Ferenc Simon; Péter Sárközy; Attila Misley, all of Budapest, Hungary

[73] Assignee: Richter Gedeon Vegyeszeti Gyar Rt., Budapest, Hungary

[21] Appl. No.: 790,856

[22] Filed: Oct. 24, 1985

[30] Foreign Application Priority Data

Oct. 25, 1984 [HU] Hungary .............................. 3976/84

[51] Int. Cl.⁴ .................. A61K 31/50; A61K 31/065; A61K 31/495
[52] U.S. Cl. ..................................... 514/249; 514/726
[58] Field of Search ................................ 514/249, 726

[56] References Cited

U.S. PATENT DOCUMENTS 4,094,908 6/1978 Toth et al. .......................... 546/241

FOREIGN PATENT DOCUMENTS 112586 7/1984 European Pat. Off. ............ 514/726

OTHER PUBLICATIONS

Merck Index, 10th Edition, Compound 1757.

*Primary Examiner*—Leonard Schenkman
*Assistant Examiner*—Joseph A. Lipovsky
*Attorney, Agent, or Firm*—Karl F. Ross; Herbert Dubno

[57] ABSTRACT

The invention relates to fodder additives comprising a compound inducing the microsomal enzyme system of the liver, preferably a compound of the formula (I)

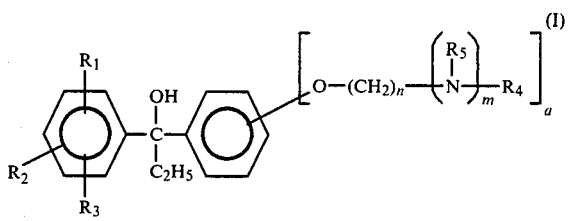

wherein $R_1$, $R_2$ and $R_3$ are identical or different and stand for hydrogen, halogen, trihalomethyl, or alkyl or alkoxy each containing from 1 to 6 carbon atoms;

$R_4$ is phenyl, dialkylaminocarbonyl or alkoxycarbonyl having from 1 to 6 carbon atoms in the alkyl and alkoxy moieties, respectively;

$R_5$ is hydrogen or methyl, or together with $R_4$ and the adjacent nitrogen atom forms a hetero-ring having up to 8 members;

n is 1, 2, 3, 4 or 5;
m is 0 or 1;
a is 0 or 1, with the proviso that if $a=0$, $R_1$ is trihalomethyl and $R_2$ and $R_3$ both are hydrogen, preferably in amount of 0.5 to 99% by weight, in an admixture with conventional carriers and/or additives and optionally at least one further active ingredient conventionally used in the animal husbandry.

The enzyme inducing compounds used according to the invention accelerate the elimination of various xenobiotics metabolizing in the liver.

9 Claims, No Drawings

FODDER ADDITIVE AND A PROCESS FOR THE PREPARATION

The invention relates to a new fodder additive and a process for the preparation of same. The invention further concerns a method for the acceleration of the elimination of veterinary or other active ingredients metabolizing in the liver from animal organisms.

It is well known that numerous veterinary preparations and products which increase the weight gain of animals can only restrictedly be used, due to their slow elimination from the organism. For example, Carbadox [active ingredient: 3-(2-quinoxalinylmethylene)-carbazic acid methyl ester N,N'-dioxide] proved to be very potent in the treatment and prophylaxis of E.coli infections and dysentery in pigs. In addition, this compound is one of the most efficious agents employed for increasing the weight gain of animals, when administered as a fodder additive. Its application is, however, strongly limited by the fact that the sanitary authorities permit its use only up to an animal weight of about 40 kg (about 90 to 100 days in case of pigs). The reason for this restriction is that this active substance is eliminated from the animals at a very low rate, therefore, it would contaminate the pork, if its application were allowed up to higher weights. Similar problems are to be faced when employing various antibiotics and other active substances as fodder additives.

Furtheron, the various contaminants are a severe problem in the animal husbandry and cause great losses in the industry. The damage caused by toxic materials accidentaly getting into the organism of animals can obviously be minimized by promoting their quick elimination.

The object of the present invention is to provide a preparation and a process by which the above problems may be eliminated or diminished.

In experiments carried out with a large number of various active substances we have surprisingly found that certain 1,1-substituted propanol derivatives are excellently suitable for the above purpose, i.e. they can successfully be used for the acceleration of the elimination of xenobiotics normally having a long waiting period. We have experimentally shown that these 1,1-substituted propanol derivatives assist the elimination of contaminating chemicals by inducing the activity of the polysubstrate monooxygenase enzyme system of the liver, and at the same time are devoid of any undesired side effect.

Accordingly, the invention relates to a fodder additive containing 0.5 to 99% by weight of a compound inducing the microsomal enzyme system of the liver, preferably a compound of the formula (I)

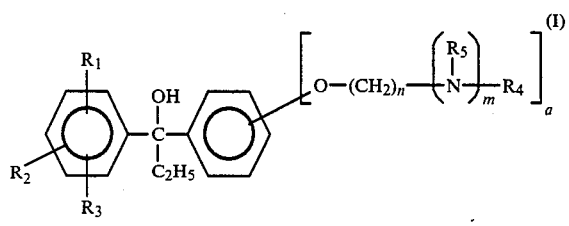

wherein $R_1$, $R_2$ and $R_3$ are identical or different and represent hydrogen, halogen, trihalomethyl, or alkyl or alkoxy each containing 1 to 6 carbon atoms;

$R_4$ is phenyl, dialkylaminocarbonyl or alkoxycarbonyl having from 1 to 6 carbon atoms in the alkyl and alkoxy moieties, respectively;

$R_5$ is hydrogen or methyl, or together with $R_4$ and the adjacent nitrogen atom forms an optionally substituted hetero-ring, having up to 8 members;

n is 1, 2, 3, 4 or 5;

m is 0 or 1;

a is 0 or 1, with the proviso that if a=0, then $R_1$ is trihalomethyl and $R_2$ and $R_3$ both are hydrogen, in admixture with conventional carriers and/or additives and optionally at least one further active ingredient used in animal husbandry.

In the common meaning of $R_4$ and $R_5$ the heterocycle may be saturated or unsaturated and may contain further heteroatoms, for example nitrogen, oxygen or sulfur atoms. As optional substituent an alkyl group can be, for example, mentioned.

The invention further relates to a process for the preparation of the above fodder additive by admixing the components specified above.

A preferred representative of the compounds of formula (I) is flumecinol [1-(3-trifluoromethylphenyl)-1-(phenyl)-propan-1-ol].

According to a still further aspect of the invention there is provided a method for the acceleration of the elimination of veterinary or other active substances metabolizing in the liver, which comprises treating the animals, following the entry of the active substances to be eliminated, preferably lipophilic xenobiotics, chlorinated aromatic hydrocarbons, plant projecting agents, with a 0.1 to 200 mg/kg of body weight dose of a compound inducing the microsomal enzyme system of the liver, preferably a compound of the formula (I), in which the substituents have the same meanings as defined above.

According to a preferred embodiment of the invention flumecinol or another enzyme inductor of the formula (I) is admixed with a fodder additive in a dose of 30 to 60 mg/kg of body weight.

The fodder additives according to the invention may contain as a veterinary active ingredient lipophilic antibiotics or substances used for increasing the weight gain of animals. Preferred antibiotics, which may be employed successfully in combination with the enzyme inductors according to the invention include e.g. chloramphenicol and oxytetracycline. Of the substances used for increasing the weight gain e.g. the elimination of Carbadox was particularly accelerated.

Carbadox or chloramphenicol is generally used in an amount of 0.001 to 50% by weight related to the total weight of the fodder additive.

Alternatively, the animals may be treated with the enzyme inducing compounds according to the invention, preferably with a compound of the formula (I), e.g. flumecinol, for 1 to 10 days, following the entry of a toxic material metabolizing in the liver, e.g. a lipophilic xenobiotic, chlorinated aromatic hydrocarbon, plant protecting agent, etc. From the active substances according to the invention a pre-mixture is prepared by means of a conventional carrier, preferably bran, which is then admixed with a premix generally used for the supplementation of standard fodder mixtures. Admixture and homogenization are carried out according to standard techniques.

In addition to bran, for example starch, talc, dried yeast and/or alga flour can be used as a carrier.

Flumecinol has first been disclosed in the Belgian Patent Specification No. 818 801, while the other compounds of the formula (I) are described in the Published European Patent Applications Nos. 116,787 and 115,205 respectively.

The preferred representatives of the compounds of formula (I), which may be used in the fodder additives and process according to the invention are as follows:
1-(4-fluorophenyl)-1-(2-benzyloxyphenyl)-propan-1-ol,
1-(2,5-dimethylphenyl)-1-(2-benzyloxyphenyl)-propan-1-ol,
1-(3-trifluoromethylphenyl)-1-[4-(diethylcarbamoylmethoxy)-phenyl]-propan-1-ol,
1-(3-chlorophenyl)-1-[2-(diethylcarbamoylmetoxy)-phenyl]-propan-1-ol,
1-(3-chlorophenyl)-1-[2-(ethoxycarbonylmethoxy)-phenyl]-propan-1-ol,
1-(3-trifluoromethylphenyl)-1-[4-/2-(piperidin-1-yl)-ethoxy/phenyl]-propan-1-ol,
1-(3-trifluoromethylphenyl)-1-[4-(2-dimethyl-aminoethoxy)-phenyl]-propan-1-ol,
1-(2-methoxyphenyl)-1-[4-(2-pyrrolidin-1-yl)-ethoxyphenyl]-propan-1-ol,
1-(4-fluorophenyl)-1-[4-(2-piperidin-1-yl)-ethoxyphenyl]-propan-1-ol.

The utility of the enzyme inducing compounds employed according to the invention is illustrated by the following test results:

1. Test animals, experimental array

Tests were carried out at a large-scale pig farm, where 25 mg/kg of body weight of Carbadox admixed with the fodder of the pigs were administered to pigs having a live weight of 40 kg. From a population fed with this fodder 27 animals, each weighing exactly 40 kg, were selected, by weighing them separately. The selected animals were railed off in a place suitable for further tests. From this time on (zero time) the animals were given the same fodder as before, except Carbadox.

The 27 animals were divided into three groups as follows:

Group I: 12 animals (ser. Nos. from 1 to 12)
  slaughtering: three animals each when starting the experiment (0 time) and on the 1st, 5th and 15th days (positive control group)
Group II: 9 amimals (ser. Nos. from 13 to 21)
  treatment: a single 40 mg/kg of body weight dose of flumecinol at zero time.
  slaughtering: three animals each on the 1st, 5th and 15th days (group treated with a single dose of flumecinol)
Group III: 6 animals (ser. Nos. 22 to 27)
  treatment: 40 mg/kg of body weight of flumecinol for three days, at zero time and on the 1st and 2nd day
  slaughtering: three animals each on the 5th and 15th days (group treated with flumecinol three times)

Flumecinol is available as a micropellet containing 19.02% of active ingredient. From this and a 1% starch hydrolysate a suspension is prepared, containing 40 mg of flumecinol per 1 ml (dose used for one kg of body weight). The active compound was administered 8 o'clock in the morning, without previous fasting, through a stomach tube, in order to ensure exact conditions for the experiments. The animals were killed and samples were taken from 8 to 11 o'clock in the morning, whereupon the samples were transported into the analytical laboratory within one hour, under cooling.

2. Test parameters and methods

Quinoxaline-2-carboxylic acid (a metabolite of Carbadox) was determined in the chop, liver and kidney tissues of three animals from each group. Each muscle and liver sample was subjected to organoleptic examination also (boiling test).

The quantity of quinoxaline-2-carboxylic acid was determined essentially following the method described in the USDA Chemistry Laboratory Guidebook (5007 Determination of Carbadox):

Following the alkaline hydrolysis of the muscle, liver and kidney samples, the hydrolysates were strongly acidified and the quinoxaline-2-carboxylic acid was extracted with ethyl acetate. The pH of the ethyl acetate extract was adjusted to 6 with a citric acid buffer, whereupon the mixture was extracted with benzene. In the next step the acid was esterified with a mixture of n-propanol and sulfuric acid, to yield propyl quinoxaline-2-carboxylate. The quantity of the latter compound was determined (after purification by thin layer chromatography) by gas chromatography. This cumbersome test procedure was always performed together with a negative control sample to which a known amount (0.2 $\mu$g–1.0 $\mu$g) of quinoxaline-2-carboxylic acid (standard) was added. The percentage of the active ingredient recovered from this sample was taken into account when calculating the residual active substance amount. In this way the error of the process was eliminated.

The test results, if not otherwise indicated, are given in $\mu$g/kg.

3. Results

The quantity of quinoxaline-2-carboxylic acid in the above-specified slaughtering times is shownn in Table 1. The tests were carried out on three animals and Table 1 contains the results obtained on the individual animals. The results were also statistically evaluated for the various sorts of tissues, although in this specific case this was not really necessary, since according to the valid prescriptions the products of animal origin should not contain Carbadox at all, i.e. the limit is zero. Therefore, we considered it more important to determine when the animal tissues become entirely Carbadox-free, than to observe the differences among the tissues of the various groups of animals in the time when they were killed.

In Table 2 the average values determined in the muscle tissue, more specifically in the ham and the longissimus muscle of the thorax are set forth. It can be seen that in the positive control group the initially rapid decrease of the amount of quinoxaline-2-carboxylic acid is gradually slowed down, and said compound is present in the muscle tissue even 15 days after the termination of Carbadox administration, in a significant amount. The test results show that the residual concentration is always higher in the chop than in the ham muscle.

The flumecinol treatment results in a significant acceleration of quinoxaline-2-carboxylic acid elimination from the muscle tissue. Already on the 5th day after the termination of Carbadox administration no residual quinoxaline-2-carboxylic acid could be detected in any of the animals treated with flumecinol. Residual Carbadox was found merely in Group II, which was given one flumecinol dose, 24 hours after treatment, but the amount found was significantly lower than in the control animals slaughtered at the same time.

In Table 3 the results concerning the liver are shown. Since the liver is the central organ of the metabolism of xenobiotics, the amount of the Carbadox metabolite residue in the liver is understandably one order of magnitude higher than in the muscle tissue. It is worthy of attention that the high initial amount in the control group is further increased on the 1st day, in spite of the fact that no further Carbadox was fed to the animals. This increase is supposedly the result of the transport of the residue from other tissues into the liver, and this additional amount is added to the metabolite concentration formed in the liver. Till the 5th day the amount of the residue in the liver is substantially decreased, but from this time on the elimination is essentially slowed down and even on the 15th day a level identical with the initial concentration in the muscles is measured.

A single 40 mg/kg of body weight dose of flumecinol results in a significant decrease in the amount of quinoxaline-2-carboxylic acid at each measuring point but this residual compound can be detected even on the 15th day.

After three subsequent treatments with flumecinol a metabolite residue can be identified on the 5th day only, but even this time in a substantially lower amount than in the control animals or in the group treated with a single dose of flumecinol.

The results set forth in Table 4 show that in the control group quinoxaline-2-carboxylic acid is detected in the kidney even on the 15th day following the termination of Carbadox addition. At the same time, in the animals which received a single dose of flumecinol no reside can be detected, although on the 15th day in the liver the presence of metabolite residue still can be detected. The values measured on the 1st and 5th days are essentially identical with the values obtained in the control group, which is not surprising at all, since the elimination of the metabolite takes place primarily through the kidney.

After the addition of flumecinol in three subsequent days no residue was detected either on the 5th or on the 15th day.

The results of the organoleptic examination (boiling test) are shown in Table 5. The results obtained are in full harmony with the results of the previous analytical measurements.

The odor observed in the control group and the absence of such problems in the group of animals treated with flumecinol (particularly in the case of three subsequent treatments) indicate that the unpleasant odor is originated from the Carbadox and not from the flumecinol. (In the liver an unpleasant odor is detected even on the 15th day.) By the flumecinol treatment the unpleasant odor can be eliminated by the 15th day, if flumecinol is applied in a single dose and by the 5th day in case of three subsequent treatments, while flumecinol as such does not result in similar undesired effects. Flumecinol is rapidly eliminated from the tissue of pigs and has no undesired effects which could be detected organoleptically.

4. Evaluation

The following conclusions can be drawn:

The muscle, kidney and liver tissues of pigs, which received a 25 mg/kg of feedstuff dose of Carbadox daily, until achieving a living weight of 40 kg, contained a significant amount of quinoxaline-2-carboxylic acid on the 15th day following the termination of Carbadox treatment.

In the animals treated with a 40 mg/kg of body weight single dose of flumecinol the muscles and the kidney become free of residue by the 5th and 15th day, respectively. In the liver the metabolite residue could be still detected on the 15th day.

The muscle tissues and the kidney of the animals treated with a 40 mg/kg of body weight daily dose of flumecinol for three subsequent days were free of residue on the 5th day, while the kidney was free of residue on the 15th day.

The flumecinol treatment eliminates the unpleasant odor which has been released in the tissues by the Carbadox administration.

In view of the above findings, flumecinol, which is a specific inductor of the polysubstrate monooxygenase enzyme system, is suitable for the acceleration of Carbadox elimination, i.e. for shortening the otherwise long waiting period until the meat of the animals and the products prepared therefrom can be consumed.

The preparation of the fodder additives according to the invention is illustrated by the following non-limiting Examples.

EXAMPLE 1

10 kg of flumecinol are admixed with 100 kg of bran and the mixture is homogenized in a suitable mixer. The premix is stored in plastic sacks.

EXAMPLE 2

2 kg of a flumecinol micropellet containing 19% of active ingredient are prepared in a pelletizing equipment. From the pellets obtained a suspension containing 40 mg of active ingredient per one ml is prepared with a 1% starch hydrolysate.

EXAMPLE 3

100 kg of XVII. standard piglet premix (manufacturer: Phylaxia, Budapest) are supplemented with 25 kg of Carbadox and 5 kg of the premix prepared according to Example 1.

The premix may contain the following ingredients: vitamins (e.g. vitamins A, $D_3$, E, K and B) pantothenic acid ester, niacin, choline chloride mineral salts: manganese, iron, zinc, copper, calcium salts, antibiotics and other antimicrobial agents, amino acids, antioxidants.

EXAMPLE 4

Essentially the procedure described in Example 1 is followed, except that the following compounds are used as active ingredient:
1-(4-fluorophenyl)-1-(2-benzyloxyphenyl)-propan-1-ol,
1-(2,5-dimethylphenyl)-1-(2-benzyloxyphenyl)-propan-1-ol,
1-(3-trifluoromethylphenyl)-1-/4-(diethylcarbamoylmethoxy)-phenyl/-propan-1-ol,
1-(3-chlorophenyl)-1-[2-(diethylcarbamoylmethoxy)-phenyl]-propan-1-ol,
1-(3-chlorophenyl)-1-[2-(ethoxycarbonylmethoxy)-phenyl]-propan-1-ol,
1-(3-trifluoromethylphenyl)-1-[4-(2-piperidin-1-yl)-ethoxyphenyl]-propan-1-ol,
1-(3-trifluoromethylphenyl)-1-[4-(2-dimethylaminoethoxy)-phenyl]-propan-1-ol,
1-(2-methoxyphenyl)-1-[4-(2-pyrrolidin-1-yl)-ethoxyphenyl]-propan-1-ol,
1-(4-fluorophenyl)-1-[4-(2-piperidin-1-yl)-ethoxyphenyl]-propan-1-ol.

TABLE 1

The influence of flumecinol treatment on the amount of quinoxaline-2-carboxylic acid in pigs (μg/kg)

| Ser. No. of animals | Treatment | 0 day muscle ham | 0 day muscle chop | 0 day liver | 0 day kidney | 1st day muscle ham | 1st day muscle chop | 1st day liver | 1st day kidney | 5th day muscle ham | 5th day muscle chop | 5th day liver | 5th day Kidney | 15th day muscle ham | 15th day muscle chop | 15th day liver | 15th day kidney |
|---|---|---|---|---|---|---|---|---|---|---|---|---|---|---|---|---|---|
| 1 | positive | 12 | 18 | 172 | 50 | | | | | | | | | | | | |
| 2 | control | 10 | 16 | 104 | 56 | | | | | | | | | | | | |
| 3 | | 12 | 20 | 120 | 62 | | | | | | | | | | | | |
| 4 | | | | | | 8 | 10 | 126 | 38 | | | | | | | | |
| 5 | | | | | | 6 | 12 | 192 | 32 | | | | | | | | |
| 6 | | | | | | 8 | 10 | 144 | 40 | | | | | | | | |
| 7 | | | | | | | | | | 4 | 8 | 32 | 12 | | | | |
| 8 | | | | | | | | | | 6 | 6 | 28 | 8 | | | | |
| 9 | | | | | | | | | | 4 | 6 | 22 | 10 | | | | |
| 10 | | | | | | | | | | | | | | 4 | 6 | 18 | 4 |
| 11 | | | | | | | | | | | | | | 2 | 4 | 12 | 6 |
| 12 | | | | | | | | | | | | | | 4 | 6 | 16 | 10 |
| 13 | one treatment | | | | | ∅ | 4 | 58 | 38 | | | | | | | | |
| 14 | with | | | | | ∅ | 6 | 64 | 30 | | | | | | | | |
| 15 | flumecinol | | | | | 4 | 6 | 72 | 24 | | | | | | | | |
| 16 | | | | | | | | | | ∅ | ∅ | 10 | 10 | | | | |
| 17 | | | | | | | | | | ∅ | ∅ | 12 | 8 | | | | |
| 18 | | | | | | | | | | ∅ | ∅ | 14 | 12 | | | | |
| 19 | | | | | | | | | | | | | | ∅ | ∅ | 8 | ∅ |
| 20 | | | | | | | | | | | | | | ∅ | ∅ | 8 | ∅ |
| 21 | | | | | | | | | | | | | | ∅ | ∅ | 6 | ∅ |
| 22 | three | | | | | | | | | ∅ | ∅ | 4 | ∅ | | | | |
| 23 | treatments | | | | | | | | | ∅ | ∅ | 6 | ∅ | | | | |
| 24 | with | | | | | | | | | ∅ | ∅ | 8 | ∅ | | | | |
| 25 | flumecinol | | | | | | | | | | | | | ∅ | ∅ | ∅ | ∅ |
| 26 | | | | | | | | | | | | | | ∅ | ∅ | ∅ | ∅ |
| 27 | | | | | | | | | | | | | | ∅ | ∅ | ∅ | ∅ |

∅: no detectable amount

TABLE 2

The quinoxaline-2-carboxylic acid content of the muscle tissue in pigs after treatment with flumecinol
(average values in μg/kg; n = 3)

| Treatment | | 0 day ham | 0 day chop | 0 day total | 1st day ham | 1st day chop | 1st day total | 5th day ham | 5th day chop | 5th day total | 15th day ham | 15th day chop | 15th day total |
|---|---|---|---|---|---|---|---|---|---|---|---|---|---|
| positive | $\bar{x}$ | 11.33 | 18.00 | 14.67 | 7.33 | 10.67 | 9.00 | 4.67 | 6.67 | 5.67 | 3.33 | 5.33 | 4.33 |
| control | s | 1.15 | 2.00 | 3.93 | 1.15 | 1.15 | 2.10 | 1.15 | 1.15 | 1.51 | 1.15 | 1.15 | 1.51 |
| | CV % | 10.15 | 11.11 | 26.79 | 15.69 | 10.78 | 23.33 | 24.63 | 17.24 | 26.63 | 34.53 | 21.58 | 34.87 |
| one treatment with flumecinol | $\bar{x}$ | N.D. | | | 1.33 | 5.33 | 3.33 | ∅ | ∅ | ∅ | ∅ | ∅ | ∅ |
| | s | | | | 2.31 | 1.15 | 2.73 | | | | | | |
| | CV % | | | | 173.68 | 21.58 | 81.98 | | | | | | |
| three treatments with flumecinol | $\bar{x}$ | N.D. | | | N.D. | | | ∅ | ∅ | ∅ | ∅ | ∅ | ∅ |
| | s | | | | | | | | | | | | |
| | CV % | | | | | | | | | | | | |

∅: no detectable amount
$\bar{x}$: average value
s: standard deviation

CV %: coefficient of variation in percent $\left(\frac{s}{\bar{x}} \cdot 100\right)$ N.D.: no data

TABLE 3

The quinoxaline-2-carboxylic acid content of the liver of pigs after treatment with flumecinol
(average values in μg/kg; n = 3)

| Treatment | | 0 day | 1st day | 5th day | 15th day |
|---|---|---|---|---|---|
| positive control | $\bar{x}$ | 132.00 | 154.00 | 27.33 | 15.33 |
| | s | 35.55 | 34.12 | 5.03 | 3.06 |
| | CV % | 26.93 | 22.16 | 18.40 | 19.96 |
| one treatment with flumecinol | $\bar{x}$ | N.D. | 64.67 | 12.00 | 7.33 |
| | s | | 7.02 | 2.00 | 1.15 |
| | CV % | | 10.86 | 16.67 | 15.69 |
| three treatments with flumecinol | $\bar{x}$ | N.D. | N.D. | 6.00 | ∅ |
| | s | | | 2.00 | |
| | CV % | | | 33.33 | |

$\bar{x}$: average value
s: standard deviation

CV %: coefficient of variation in percent $\left(\frac{s}{\bar{x}} \cdot 100\right)$ ∅: no detectable amount
N.D.: no data

TABLE 4

The quinoxaline-2-carboxylic acid content of the kidney of pigs after treatment with flumecinol
(average values in μg/kg; n = 3)

| Treatment | | 0 day | 1st day | 5th day | 15th day |
|---|---|---|---|---|---|
| positive | $\bar{x}$ | 56.00 | 36.67 | 10.00 | 6.67 |
| control | s | 6.00 | 4.16 | 2.00 | 3.06 |
|  | CV % | 10.71 | 11.34 | 20.00 | 45.88 |
| one treat- | $\bar{x}$ | N.D. | 30.67 | 10.00 | ∅ |
| ments with | s |  | 7.02 | 2.00 |  |
| flumecinol | CV % |  | 22.89 | 20.00 |  |
| three treat- | $\bar{x}$ | N.D. | N.D. | ∅ | ∅ |
| ments with |  |  |  |  |  |
| flumecinol |  |  |  |  |  |

∅: no detectable amount
$\bar{x}$: average value
s: standard deviation

CV %: coefficient of variation in percent $\left(\frac{s}{\bar{x}} \cdot 100\right)$ N.D.: no data

TABLE 5

The results of visual observation of the muscle and liver tissues in pigs treated with Carbadox and flumecinol

| Ser. No. of animals | Treatment | 0 day muscle ham | 0 day muscle chop | 0 day liver | 1st day muscle ham | 1st day muscle chop | 1st day liver | 5th day muscle ham | 5th day muscle chop | 5th day liver | 15th day muscle ham | 15th day muscle chop | 15th day liver |
|---|---|---|---|---|---|---|---|---|---|---|---|---|---|
| 1 | positive | 2 | 2 | 4 | | | | | | | | | |
| 2 | control | 2 | 2 | 4 | | | | | | | | | |
| 3 | | 2 | 2 | 4 | | | | | | | | | |
| 4 | | | | | 2 | 1 | 4 | | | | | | |
| 5 | | | | | 1 | 2 | 4 | | | | | | |
| 6 | | | | | 2 | 1 | 4 | | | | | | |
| 7 | | | | | | | | 1 | 1 | 3 | | | |
| 8 | | | | | | | | 1 | 1 | 3 | | | |
| 9 | | | | | | | | 1 | 1 | 2 | | | |
| 10 | | | | | | | | | | | 1 | 1 | 3 |
| 11 | | | | | | | | | | | 1 | 1 | 2 |
| 12 | | | | | | | | | | | 1 | 1 | 2 |
| 13 | one treat- | | | | 1 | 1 | 3 | | | | | | |
| 14 | ment | | | | 1 | 1 | 3 | | | | | | |
| 15 | with | | | | 1 | 1 | 3 | | | | | | |
| 16 | flumecinol | | | | | | | 1 | 1 | 2 | | | |
| 17 | | | | | | | | 1 | 1 | 2 | | | |
| 18 | | | | | | | | 1 | 1 | 2 | | | |
| 19 | | | | | | | | | | | 1 | 1 | 1 |
| 20 | | | | | | | | | | | 1 | 1 | 1 |
| 21 | | | | | | | | | | | 1 | 1 | 1 |
| 22 | three treat- | | | | | | | 1 | 1 | 1 | | | |
| 23 | ments with | | | | | | | 1 | 1 | 1 | | | |
| 24 | flumecinol | | | | | | | 1 | 1 | 1 | | | |
| 25 | | | | | | | | | | | 1 | 1 | 1 |
| 26 | | | | | | | | | | | 1 | 1 | 1 |
| 27 | | | | | | | | | | | 1 | 1 | 1 |

1 = negative
2 = slight strange (indeterminable) odor
3 = some strange (slight medicament-like) odor
4 = definite strange (more expressed medicament) odor

We claim:

1. A method of preventing buildup of quinoxaline-2-carboxylic acid metabolite of carbadox in an animal subject which comprises the steps of:
    feeding a fodder containing carbadox to said animal subject, whereby quinoxaline-2-carboxylic acid metabolite of carbadox accumulates in the liver of the animal subject with time; and
    promoting elimination of said quinoxaline-2-carboxylic acid metabolite of carbadox from the liver of said animal subject by administering to said animal subject an effective amount of the compound of the Formula (I)

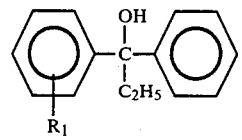

wherein $R_1$ is trihalomethyl.

2. The method defined in claim 1 wherein said carbadox and said compound are administered to said subject simultaneously in admixture with said fodder.

3. The method defined in claim 1 wherein the compound of the Formula (I) is flumecinol.

4. The method defined in claim 1 wherein the compound of the Formula (I) is administered in a dosage of 0.1 to 200 mg/kg of body weight.

5. The method defined in claim 1 wherein the compound of the Formula (I) is administered in a dosage of 30 to 60 mg/kg of body weight.

6. The method defined in claim 1 wherein the compound of the Formula (I) is administered for 1 to 10 consecutive days.

7. The method defined in claim 1 wherein the animal subject is a pig.

8. A fodder additive which comprises 0.5 to 99% by weight of a compound of the Formula (I)

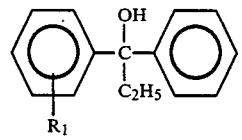

wherein $R_1$ is trihalomethyl; and
0.001 to 50% by weight of carbadox in admixture with a veterinarily acceptable inert carrier.

9. The fodder additive defined in claim 8 wherein the compound of the Formula (I) is flumecinol.

* * * * *